(12) United States Patent
Persoons et al.

(10) Patent No.: US 6,944,492 B1
(45) Date of Patent: Sep. 13, 2005

(54) PATIENT BED SUPPORT FOR AN OPEN MRI SYSTEM

(75) Inventors: James J. Persoons, East Northport, NY (US); Jevan Damadian, East Northport, NY (US); William H. Wahl, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 453 days.

(21) Appl. No.: 10/177,625

(22) Filed: Jun. 20, 2002

Related U.S. Application Data

(60) Provisional application No. 60/326,363, filed on Oct. 1, 2001.

(51) Int. Cl.[7] .......................................... A61B 5/055
(52) U.S. Cl. ........................................ 600/415; 5/601
(58) Field of Search ....................... 600/415; 324/318, 324/319; 5/300, 301, 600, 601; 378/209

(56) References Cited

U.S. PATENT DOCUMENTS

| | | | |
|---|---|---|---|
| 4,534,358 A | 8/1985 | Young ......................... | 128/653 |
| 4,608,991 A | 9/1986 | Rollwitz ...................... | 128/653 |
| 4,613,820 A | 9/1986 | Edelstein et al. ............ | 324/318 |
| 4,629,989 A | 12/1986 | Riehl et al. .................. | 324/318 |
| 4,651,099 A | 3/1987 | Vinegar et al. .............. | 324/320 |
| 4,668,915 A | 5/1987 | Daubin et al. ............... | 324/309 |
| 4,707,663 A | 11/1987 | Minkoff et al. .............. | 324/319 |
| 4,766,378 A | 8/1988 | Danby et al. ................. | 324/307 |
| 4,777,464 A | 10/1988 | Takabatashi et al. ......... | 335/306 |
| 4,805,626 A | 2/1989 | DiMassimo et al. | |
| 4,829,252 A | 5/1989 | Kaufman ...................... | 324/309 |
| 4,875,485 A | 10/1989 | Matsutani .................... | 128/653 |
| 4,968,937 A | 11/1990 | Akgun ......................... | 324/318 |
| 4,985,678 A | 1/1991 | Gangarosa et al. ......... | 324/318 |
| 5,008,624 A | 4/1991 | Yoshida ....................... | 324/318 |
| 5,061,897 A | 10/1991 | Danby et al. ................ | 324/318 |
| 5,065,761 A | 11/1991 | Pell ........................ | 128/660.03 |
| 5,122,363 A | 6/1992 | Balkus, Jr. et al. | |
| 5,124,651 A | 6/1992 | Danby et al. ................ | 324/318 |
| 5,128,121 A | 7/1992 | Berg et al. | |
| 5,153,546 A | 10/1992 | Laskaris ...................... | 335/216 |
| 5,162,768 A | 11/1992 | McDougall et al. ......... | 335/296 |
| 5,194,810 A | 3/1993 | Breneman et al. ........... | 324/319 |
| 5,197,474 A | 3/1993 | Englund et al. .......... | 128/653.5 |
| 5,207,224 A | 5/1993 | Dickinson et al. ....... | 128/653.5 |
| 5,229,723 A | 7/1993 | Sakurai et al. .............. | 324/319 |
| 5,250,901 A | 10/1993 | Kaufman et al. ............ | 324/318 |
| 5,291,890 A | 3/1994 | Cline et al. .............. | 128/653.2 |
| 5,305,749 A | 4/1994 | Li et al. ................... | 128/653.2 |
| 5,315,276 A | 5/1994 | Huson et al. ................ | 335/216 |
| 5,382,904 A | 1/1995 | Pissanetzky ................. | 324/319 |

(Continued)

OTHER PUBLICATIONS

Niendorf, H P., et al., "Safety and tolerance after intravenous administration of 0.3 mmol/kg Gd-DTPA, Results of a randomized, controlled clinical trial.". *Investigative Radiology, 26 Suppl 1*, S221-3; discussion S232-5, (1991), S221-5.

(Continued)

*Primary Examiner*—Shawna J. Shaw
(74) *Attorney, Agent, or Firm*—Schwegman, Lundberg, Woessner & Kluth, P.A.

(57) ABSTRACT

A patient bed support for maneuvering a patient in an open MRI system that includes an upper pole assembly and a lower pole assembly. The patient bed support includes a frame for attaching the patient bed support to the lower pole assembly in the MRI system and a member movably attached to the frame such that a patient placed on the member may be moved relative to the lower and upper pole assemblies of the MRI system.

16 Claims, 8 Drawing Sheets

U.S. PATENT DOCUMENTS

| | | | |
|---|---|---|---|
| 5,412,363 A | 5/1995 | Breneman et al. | 335/216 |
| 5,423,315 A | 6/1995 | Margosian et al. | |
| 5,436,607 A | 7/1995 | Chari et al. | 335/216 |
| 5,460,799 A | 10/1995 | Elgavish et al. | |
| 5,490,513 A | 2/1996 | Damadian et al. | 128/653.2 |
| 5,519,372 A | 5/1996 | Palkovich et al. | 335/216 |
| 5,592,090 A | 1/1997 | Pissanetzky | 324/319 |
| 5,606,970 A | 3/1997 | Damadian | 128/653.2 |
| 5,697,164 A * | 12/1997 | Hausmann et al. | 33/512 |
| 5,735,278 A | 4/1998 | Hoult et al. | 128/653.2 |
| 5,779,637 A | 7/1998 | Palkovich et al. | |
| 5,899,859 A * | 5/1999 | Votruba et al. | 600/415 |
| 6,011,396 A * | 1/2000 | Eckels et al. | 324/319 |
| 6,141,579 A | 10/2000 | Bonutti | |
| 6,236,210 B1 * | 5/2001 | Takekoshi et al. | 324/319 |
| 6,278,274 B1 * | 8/2001 | Biglieri et al. | 324/318 |
| 6,311,082 B1 | 10/2001 | Creighton, IV et al. | |
| 6,345,193 B2 * | 2/2002 | Dutto et al. | 600/415 |
| 6,377,830 B1 * | 4/2002 | Carrozzi et al. | 600/407 |
| 6,385,481 B2 | 5/2002 | Nose et al. | |
| 6,504,371 B1 * | 1/2003 | Damadian et al. | 324/318 |
| 2001/0012914 A1 | 8/2001 | Kuth et al. | 600/415 |
| 2003/0062698 A1 * | 4/2003 | Imai et al. | 324/318 |
| 2004/0186374 A1 * | 9/2004 | Satragno et al. | 600/415 |

OTHER PUBLICATIONS

Oldendorf, William H., et al., "Brain extracellular space and the sink action of cerebrospinal fluid", *Archives of Neurology, 17*, (1967), 196-205.

* cited by examiner

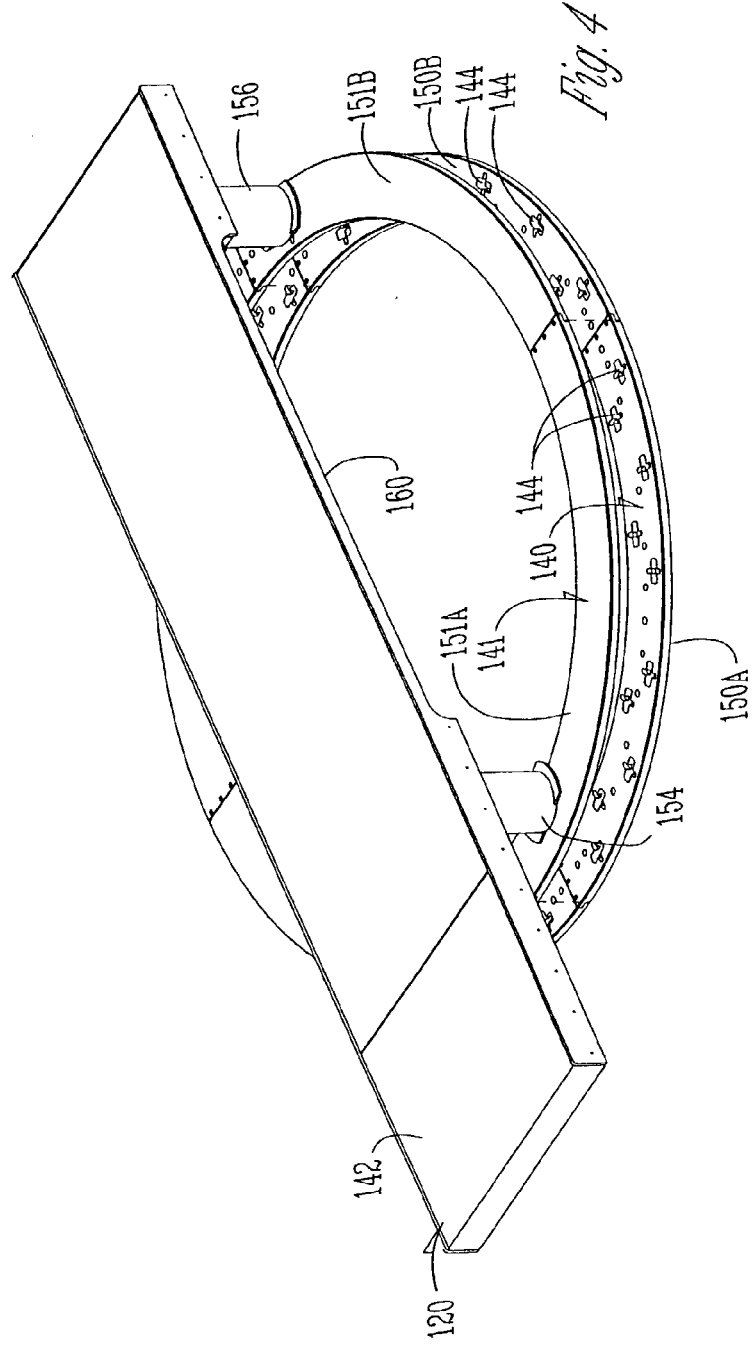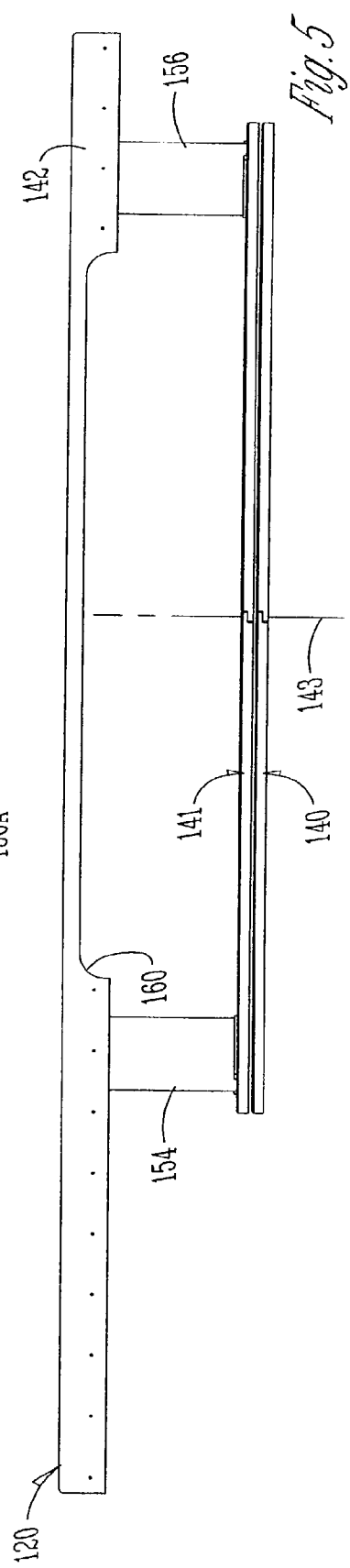

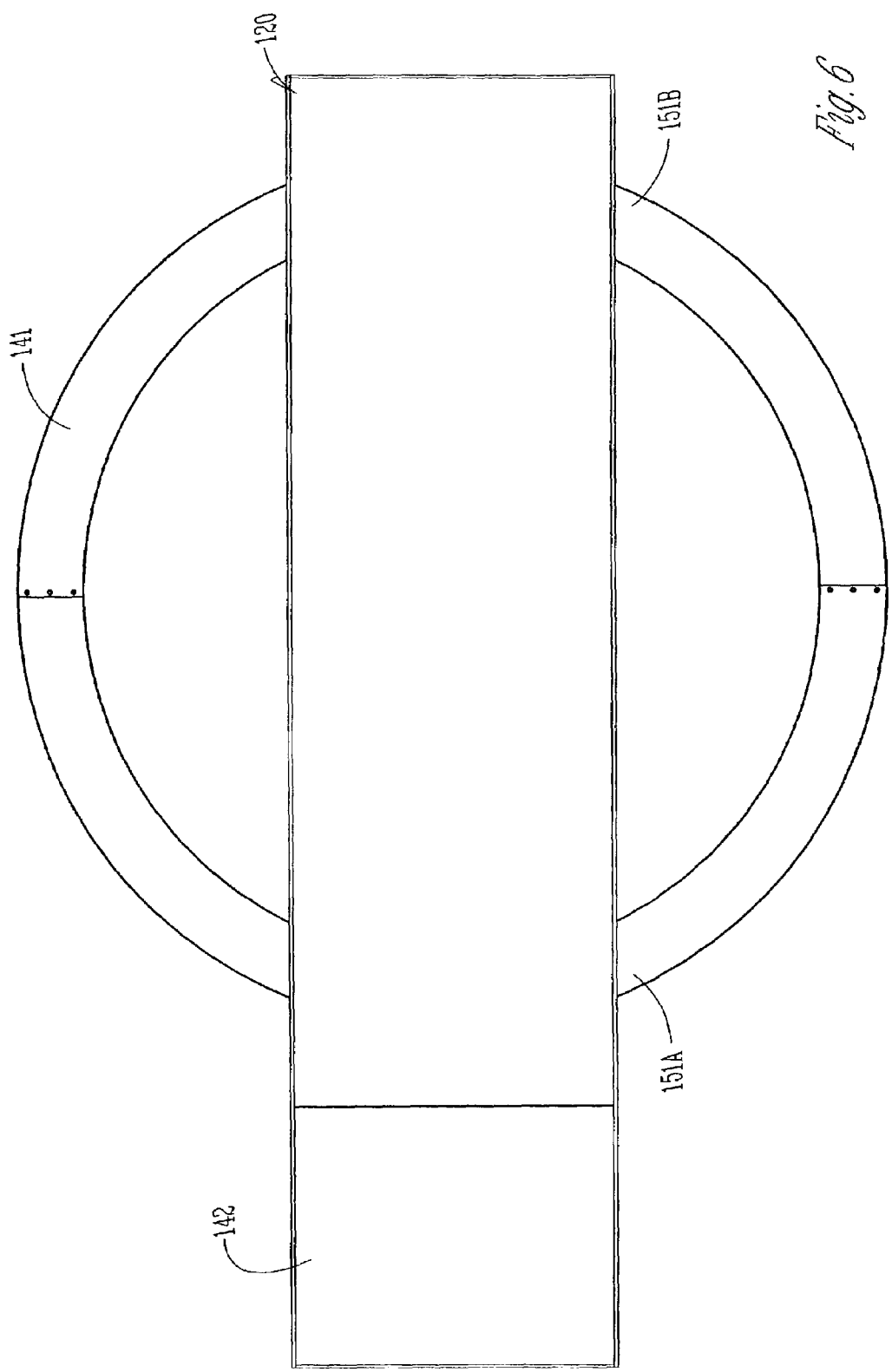

PATIENT BED SUPPORT FOR AN OPEN MRI SYSTEM

CROSS-REFERENCE TO RELATED APPLICATION

This application claims priority to U.S. Provisional Application Ser. No. 60/326,363 filed Oct. 1, 2001, which application is incorporated herein by reference.

FIELD OF THE INVENTION

The present invention relates to MRI systems, and more specifically to a patient bed support that positions patients within an open MRI system.

BACKGROUND

Patients seeking medical treatment typically need to be positioned correctly in order to properly receive diagnosis or treatment. One example is in magnetic resonance imaging (MRI) systems that scan portions of a patient's anatomy within a relatively small imaging volume.

One example of an open MRI system is the FONAR 360° system designed by Fonar Corporation. Another example is the OR-360™ (MRI Operating Room), also designed by Fonar Corporation. FONAR 360° systems include magnetic poles that are part of a FONAR 360° scanner. The poles are typically located in the approximate center of a room with one pole protruding from the ceiling and the other pole protruding from the floor. The patient is positioned in the space, or gap, between the two poles and is accessible from virtually any angle. The patient can be placed on his back, stomach or side. A large portion of the MRI system may be located outside the scanning room such that primarily the patient is exposed to the main magnetic field.

FIG. 1 illustrates a portion of an example open MRI system 10. MRI system 10 includes a magnet 11. Magnet 11 includes an upper pole assembly 12 and a lower pole assembly 14 with a gap 16 between the upper and lower pole assemblies 12, 14.

A scanning operation is typically done by positioning a patient bed 17 (which includes a patient) within gap 16 (note arrow X) between upper and lower pole assemblies 12, 14. One type of patient bed 17 includes a frame that is made up a slab 18 and four legs 19 that support slab 19. Each leg 19 typically includes a roller or caster 20 for rolling bed 17 across the floor. The space under slab 18 and between legs 19 is large enough to receive lower pole assembly 14 when patient bed 17 is moved into gap 16.

SUMMARY OF THE INVENTION

The present invention relates to a patient bed support for maneuvering a patient in an open MRI system that includes an upper pole assembly and a lower pole assembly. The patient bed support includes a frame for attaching the patient bed support to the lower pole assembly in the MRI system and a member movably attached to the frame to maneuver patients that are placed on the member relative to the lower and upper pole assemblies of the MRI system.

In another example embodiment, the present invention relates to a patient bed support for maneuvering a patient in an MRI system that includes an upper pole assembly and a lower pole assembly. The patient bed support includes a first ring that is used to couple the patient bed support to the lower pole assembly in the MRI system and a second ring rotatably attached to the first ring. The patient bed support further includes a platform that supports a patient during scanning within the MRI system. The platform is coupled to the second ring such that the patient is maneuvered within the MRI system by rotating the second ring relative to the first ring.

The present invention also relates to an MRI system that includes a lower pole assembly, an upper pole assembly and a patient bed support between the upper and lower pole assemblies. The patient bed support includes a frame that is coupled to the lower pole assembly and a member that is movably coupled to the frame. The member is moved relative to the lower pole assembly of the MRI system in order to accurately position patients within the MRI system.

A patient bed support for patient handling and positioning has been devised which is faster, more accurate, and more flexible in positioning patients in open MRI systems. The patient bed support attaches to a lower pole assembly and bears the weight of a patient bed that is positioned above the lower pole assembly during a scanning procedure. In some embodiments, the patient bed support rotates to allow the patient to be positioned in various orientations between the upper and lower pole assemblies of the MRI magnet.

The MRI system may be used in conjunction with a patient bed that includes casters for rolling the patient bed across a floor toward a lower pole assembly that has 360 degree access around it. The bed is sized to allow it to be rolled over the patient bed support that is mounted on the lower pole assembly. The patient bed support may also include means for raising the patient bed such that the bed can swivel freely.

BRIEF DESCRIPTION OF THE DRAWINGS

FIG. 4 is a perspective view of a patient bed support embodying the present invention.

FIG. 5 is a top view of the patient bed support shown in FIG. 4.

FIG. 6 is a side view of the patient bed support shown in FIG. 4.

DETAILED DESCRIPTION

In the following detailed description, reference is made to the accompanying drawings that show specific embodiments in which the invention may be practiced. It is understood that other embodiments may be utilized and structural changes may be made without departing from the scope of the present invention.

Figure 1:
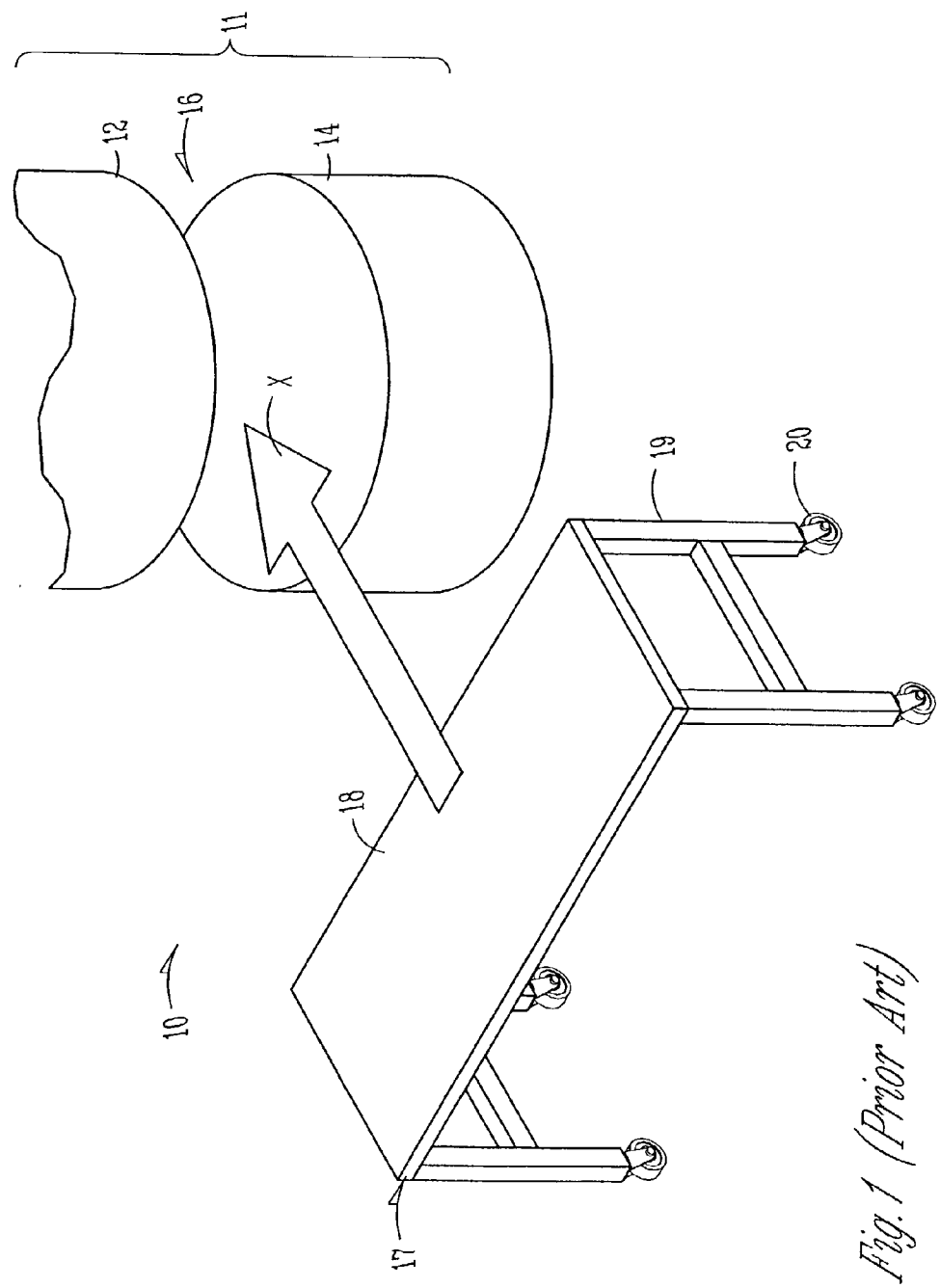
FIG. 1 is a perspective view illustrating a portion of a prior art MRI system.
Figure 2:
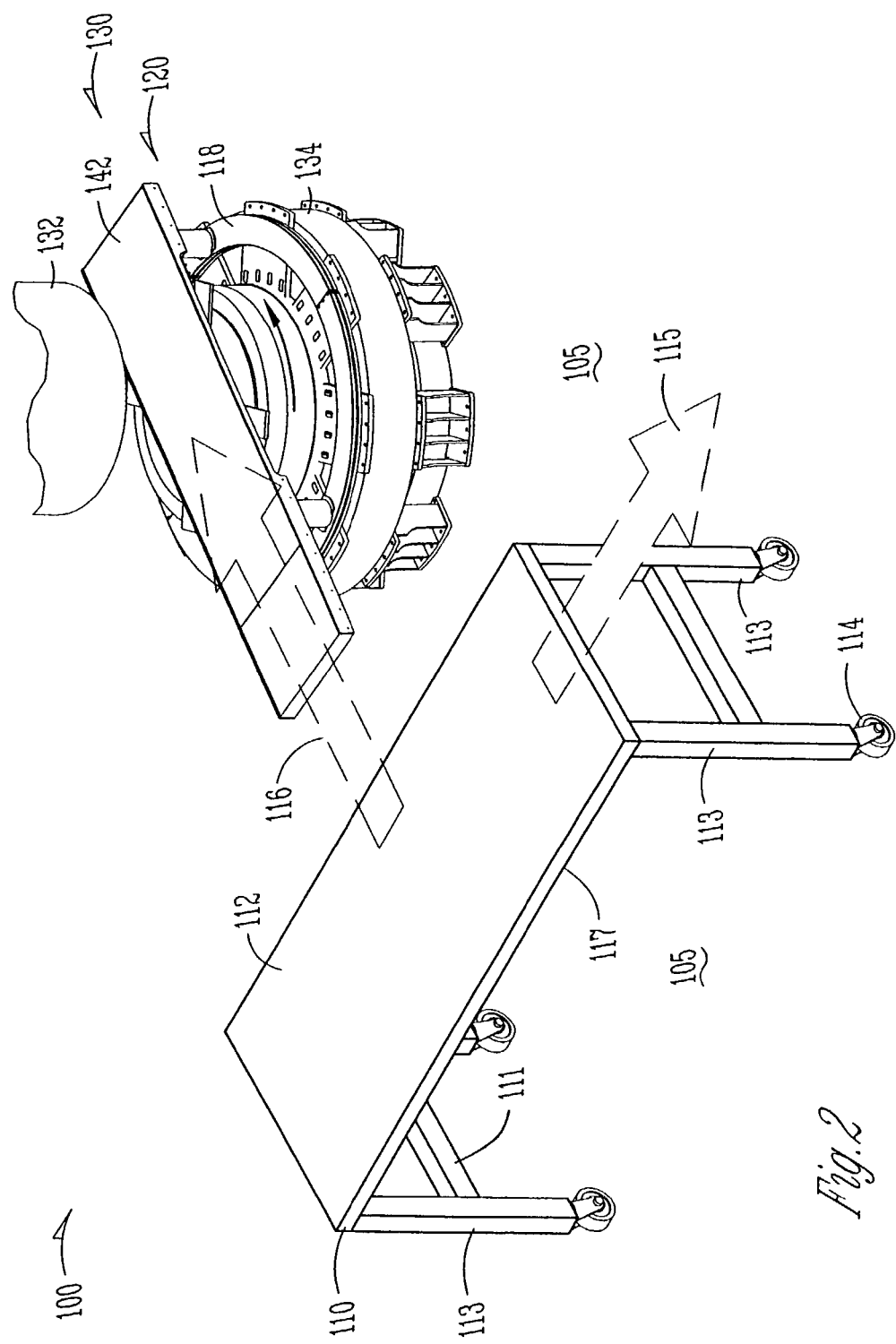
FIG. 2 is a perspective view illustrating a portion of an MRI system embodying the present invention.
Figure 3:
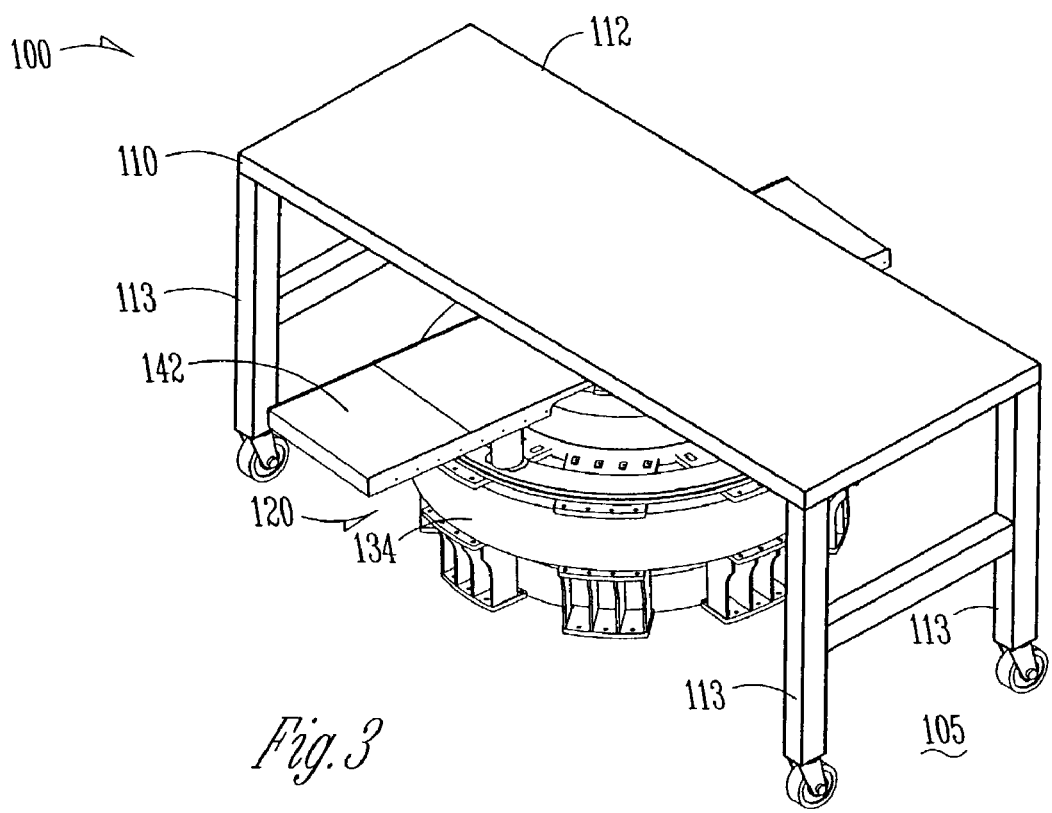
FIG. 3 is a perspective view of the portion shown in FIG. 2 with a bed positioned on a lower pole assembly of the MRI system.

FIGS. 2 and 3 show a patient bed positioner 120 embodying the present invention that is utilized in portion 130 of an MRI system embodying the present invention. MRI system 130 includes a magnet which is made up of an upper pole assembly 132 and a lower pole assembly 134. Patient bed support 120 is attached to lower pole assembly 134 such that patient bed support 120 is positioned within a gap 136 between the upper and lower pole assemblies 132, 134. Upper pole assembly 132 is not shown in FIG. 3 for purposes of clarity.

MRI system 130 is used in conjunction with a patient bed 110 that includes a frame 111 having four legs 113. Each leg 113 includes a roller or caster 114 at an end thereof for rolling bed 110 across a floor 105. Grooves (not shown) can be provided in floor 105 to guide bed 110 as it is being rolled into MRI system 130.

A slab 112 may be located on top of bed 110. As indicated by arrow 115, slab 112 may be configured to translate linearly along the length of bed 110 to more accurately position the patient within gap 136. Portion 130 may also include sensors and controllers that are used to even more precisely position slab 112.

Patient bed support 120 is configured to be coupled to lower pole assembly 134. In one embodiment, patient bed support 120 rises up in a vertical direction relative to the floor 105 and rotate in the same plane as the floor. Patient bed support 120 may be made from plastic, composite, ceramic, or other non-metallic or non-magnetic materials. It can be driven via a screw drive, a scissor lift or other equivalent means, such as pneumatic and hydraulic. Patient bed support 120 may also be driven by servo-motors that precisely drive and control the position of patient bed support 120.

When a patient is to be scanned, patient bed 110 (which includes a patient thereon) is rolled over the lower pole assembly 134 and patient bed support 120 as indicated by arrow 116. The bed is sized so that there is clearance between a bottom 117 of bed 110 and patient bed support 120. When bed 110 is properly positioned within the magnet, patient bed support 120 is raised. Patient bed support 120 contacts a bottom surface 117 of patient bed 110 and lifts bed 110 off of the floor 105. The weight of the bed is transferred from the floor to patient bed support 120. Slab 112 may be a separable part of patient bed 110 such that slab 112 is the only part of bed 110 which is lifted.

Once bed 110 has been lifted, it is then freely rotatable on top of the bottom patient bed support. This allows medical personal to position the bed and move around the bed as needed. Sensors may be used to monitor the rotation of the bed such that an operator can use computer controls to position a patient. The associated computer may also be able to configure the corresponding MRI scans on a monitor or print-out. When the MRI procedure is completed, patient bed support 120 is lowered down to its original position and the patient bed 110 is rolled out of the scanner. Bed 110 may be rolled out of the same side of the magnet as where it entered, rolled out the other side to provide more efficient use of the scanner, and/or rolled out of the scanner in any direction.

Open MRI systems allow a patient to be positioned upon a bed in a dressing room, and then rolled into the scanner room. Patient beds can be inserted from any direction because of the 360 degrees access provided by open MRI systems.

Although FIGS. 2 and 3 show platform 142 oriented transversely to slab 112 on patient bed 110 for purposes of clarity, platform 142 is preferably oriented so that it is entirely under slab 112. Positioning platform 142 under slab 112 prevents platform 142 from inhibiting medical personnel as they maneuver around a patient during scanning and surgical procedures. In other example embodiments, the size and shape of platform 142 is modified to maintain platform 142 under patient bed 110.

FIGS. 4–6 illustrate an example embodiment of patient bed support 120. Patient bed support 120 includes a frame, such as first ring 140, that is used to couple patient bed support 120 to the lower pole assembly 134 in the MRI system. Patient bed support 120 also includes a member, such as second ring 141, that is movably attached to first ring 140. In some embodiments, bearings 144 are between first and second rings 140, 141 to facilitate rotating second ring 141 relative to first ring 140.

Patient bed support 120 may further include a platform 142 that supports a patient (not shown) during scanning within the MRI system. Platform 142 is coupled to second ring 141 such that the patient can be maneuvered within the MRI system by rotating second ring 141 relative to first ring 140.

Figure 7:
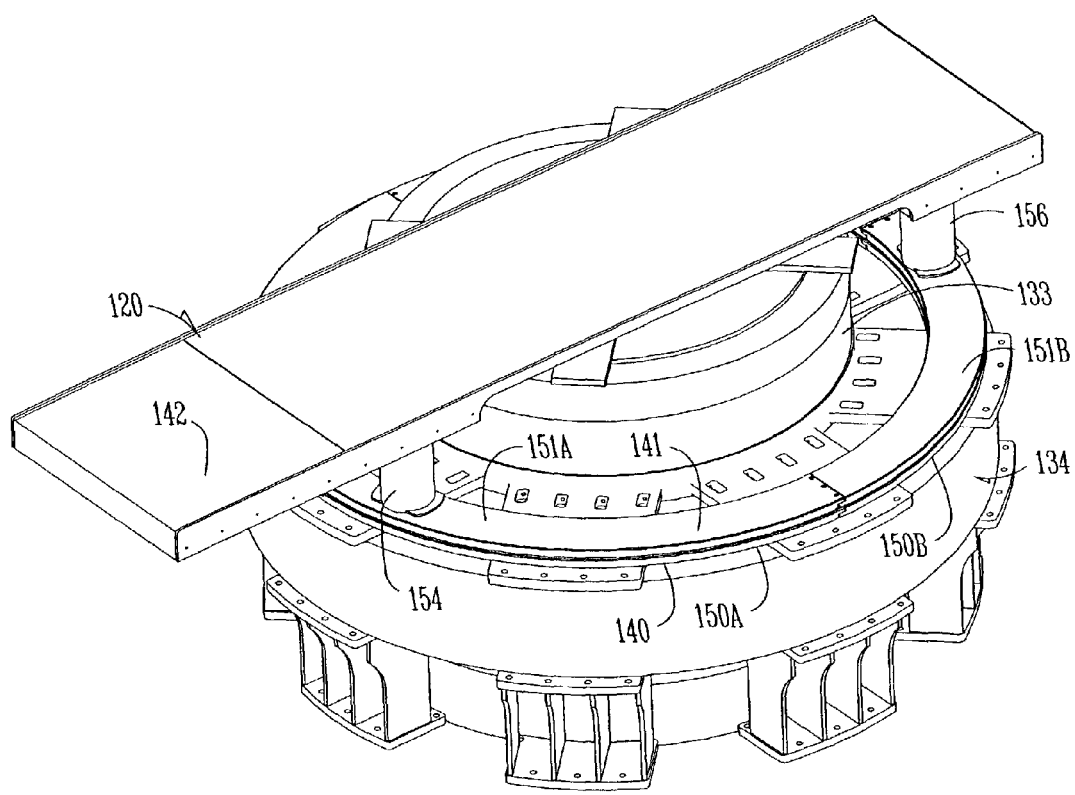
FIG. 7 is a perspective view of a patient bed support shown in FIGS. 4–6 assembled onto a lower pole assembly.
Figure 8:
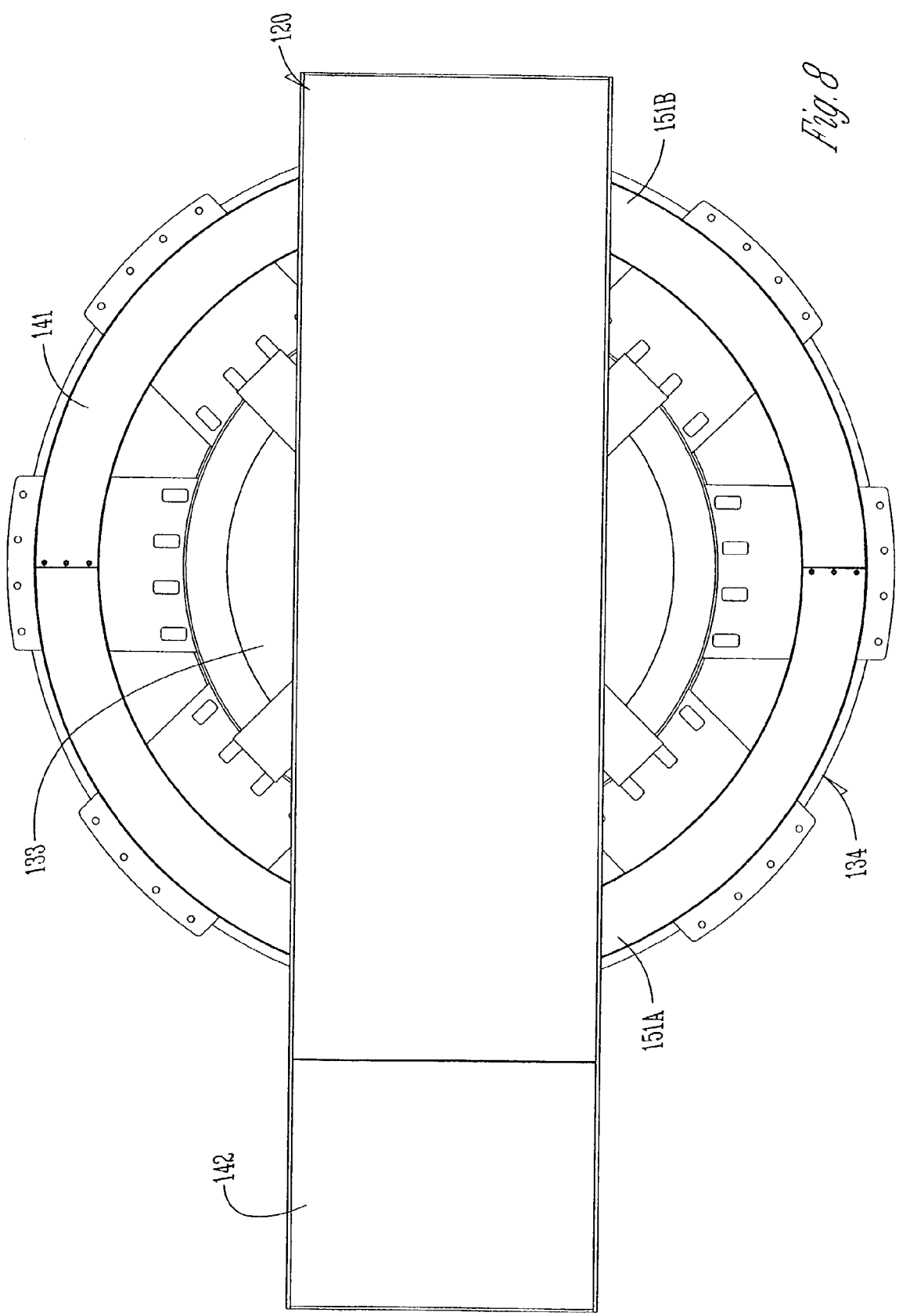
FIG. 8 is a top view of the patient bed support and lower pole assembly shown in FIG. 7.
Figure 9:
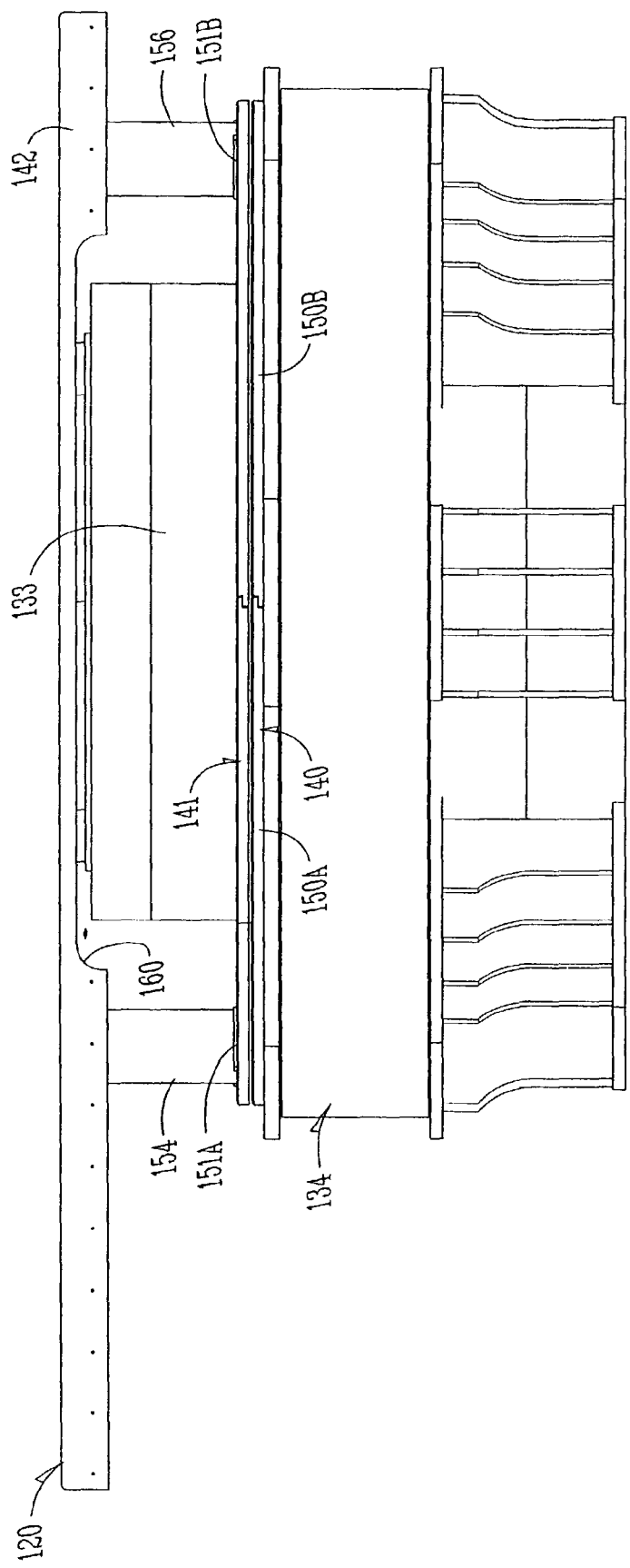
FIG. 9 is a side view of the patient bed support and lower pole assembly shown in FIG. 7.

In some embodiments, first and second ring 140, 141 are sized large enough to be positioned around an upper portion 133 of lower pole assembly 134 (see FIGS. 7–9) such that first and second rings 140, 141 are substantially horizontal when coupled to lower pole assembly 134. First ring 140 and second ring 141 have a common longitudinal axis 143 (see FIG. 5) such that second ring 142 rotates about longitudinal axis 143.

First ring 140 may be formed from a first semi-circular section 150A and a second semi-circular section 150B that are coupled together to form first ring 140. In addition, second ring 141 may be formed from a third semi-circular section 151A and a fourth semi-circular section 151B that are coupled together to form second ring 141. In other embodiments, first and second rings 140, 141 may be formed from more than two at least partially circular sections. In still other embodiments, first and second rings 140, 141 may be combined into a single ring.

In the illustrated example embodiment, one or more supports 154 extend from one side of second ring 141, such as from third semi-circular section 151A, and one or more supports 156 extend from an opposing side of second ring 141, such as from fourth semi-circular section 151B.

Platform 142 may be coupled to second ring 141 by securing platform 142 to supports 154, 156 via any conventional means. One or more of the supports 154, 156 may include lifting means such that supports 154 can tilt platform 142 and/or maneuver platform vertically. It should be noted that any combination of supports may be used to couple platform 142 to second ring 141 depending on the configuration of platform 142 and second ring 141.

Platform 142 may include a recessed section 160 that is adapted to receive upper portion 133 of lower pole assembly 134 when patient bed support 120 is mounted to lower pole assembly 134. Recessed section 160 permits platform 142 to rotate freely about upper portion 133 of lower pole assembly 134 as second ring 141 rotates relative to first ring 140.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A patient bed support for maneuvering a patient in an open MRI system that includes an upper pole assembly and a lower pole assembly, the patient bed support comprising:

a frame attaching the patient bed support to the lower pole assembly in the MRI system;

a member movably attached to the frame to maneuver patients that are placed on the member relative to the lower and upper pole assembly of the MRI system, wherein the member rotates relative to the frame and the frame is a first ring and the member is a second ring, the first and second rings being sized in order to position the first and second rings around an upper portion of the lower pole assembly.

2. The patient bed support of claim 1, wherein the first ring and the second ring have a common longitudinal axis.

3. The patient bed support of claim 2, wherein the second ring rotates about the longitudinal axis of the first and second rings.

4. The patient bed support of claim 2, wherein the first ring includes a first semi-circular section and a second semi-circular section that are coupled together to form the first ring.

5. The patient bed support of claim 4, wherein the second ring includes a third semi-circular section and a fourth semi-circular section that are coupled together to form the second ring.

6. The patient bed support of claim 1, further comprising bearings between the first and second rings to facilitate rotating the second ring relative to the first ring.

7. The patient bed support of claim 1, wherein the first and second rings are substantially horizontal when attached to the lower pole assembly of the MRI system.

8. The patient bed support of claim 1, further comprising one or more supports extending from opposing sides of the second ring, and a platform extending between the supports to receive a patient to be analyzed using the MRI system.

9. The patient bed support of claim 8, wherein one set of two supports extends from one side of the second ring, and another set of two supports extends from an opposing side of the second ring.

10. The patient bed support of claim 8, wherein at least one of the supports includes lifting means to maneuver the platform relative to the second ring.

11. The patient bed support of claim 8, wherein the platform includes a recessed section that receives the upper portion of the lower pole assembly when the patient bed support is mounted to the lower pole assembly.

12. A patient bed support for maneuvering a patient in an open MRI system that includes an upper pole assembly and a lower pole assembly, the patient bed support comprising:

a first ring attaching the patient bed support to the lower pole assembly in the MRI system;

a second ring rotatably attached to the first ring;

a platform for receiving patients that are to be analyzed by the MRI system, the platform engaged with the second ring such that the patient is maneuvered within the MRI system by rotating the second ring relative to the first ring.

13. The patient bed support of claim 12, wherein the first and second rings are sized in order to position the first and second rings around an upper portion of the lower pole assembly.

14. The patient bed support of claim 12, wherein the first ring and the second ring have a common longitudinal axis and the second ring rotates about the longitudinal axis of the first and second rings.

15. An MRI system comprising:

a lower pole assembly;

an upper pole assembly positioned above the lower pole assembly; and a patient bed support between the upper and lower pole assemblies, the patient bed support including a frame coupled to the lower pole assembly and a member movably attached to the frame, wherein the frame is a first ring and the member is a second ring having a common longitudinal axis with the first ring such that the second ring rotates relative to the first ring around the longitudinal axis, the first and second rings being sized in order to position the first and second rings around an upper portion of the lower pole assembly.

16. The patient bed support of claim 15, wherein the first and second rings are substantially horizontal when the first ring is attached to the lower pole assembly of the MRI system, and further comprising a platform coupled to opposing sides of the second ring such that the platform rotates along with the second ring relative to the upper and lower pole assemblies in the MRI system.

* * * * *